United States Patent
Welz (10) Patent No.: US 8,758,210 B2
(45) Date of Patent: Jun. 24, 2014

(54) APPARATUS FOR PERFORMING A CENTRIFUGAL FIELD-FLOW FRACTIONATION COMPRISING A SEAL AND METHOD

(75) Inventor: Roland Welz, Schongau (DE)

(73) Assignee: Postnova Analytics GmbH, Landsberg (DE)

( * ) Notice: Subject to any disclaimer, the term of this patent is extended or adjusted under 35 U.S.C. 154(b) by 0 days.

(21) Appl. No.: 13/821,237

(22) PCT Filed: May 21, 2012

(86) PCT No.: PCT/EP2012/059350
§ 371 (c)(1),
(2), (4) Date: Mar. 6, 2013

(87) PCT Pub. No.: WO2012/160018
PCT Pub. Date: Nov. 29, 2012

(65) Prior Publication Data
US 2014/0066280 A1    Mar. 6, 2014

(30) Foreign Application Priority Data

May 20, 2011   (EP) .................................... 11166874

(51) Int. Cl.
*B04B 7/00*   (2006.01)
(52) U.S. Cl.
USPC .................. 494/23; 494/37; 494/41; 494/45; 277/304; 277/927
(58) Field of Classification Search
USPC ....................... 494/23–27, 37, 38–41, 43, 45; 210/360.1, 380.1; 277/304, 926, 927
See application file for complete search history.

(56) References Cited

U.S. PATENT DOCUMENTS

| | | | | |
|---|---|---|---|---|
| 3,698,626 A | | 10/1972 | Kotrappa et al. | |
| 3,724,748 A | * | 4/1973 | Jacobson | 494/11 |
| 3,759,591 A | * | 9/1973 | Wright et al. | 384/481 |
| 4,283,276 A | * | 8/1981 | Grant | 209/155 |
| 4,284,497 A | * | 8/1981 | Grant | 209/155 |
| 4,285,809 A | * | 8/1981 | Dilks et al. | 209/155 |
| 4,285,810 A | * | 8/1981 | Kirkland et al. | 209/155 |
| 4,353,795 A | * | 10/1982 | Romanauskas | 209/155 |
| 4,356,083 A | * | 10/1982 | Romanauskas | 209/155 |
| 4,357,235 A | * | 11/1982 | Dilks, Jr. | 209/155 |
| 4,375,871 A | * | 3/1983 | Romanauskas | 494/41 |
| 4,414,106 A | * | 11/1983 | Romanauskas | 209/155 |
| 4,446,014 A | * | 5/1984 | Dilks et al. | 209/155 |
| 4,446,015 A | * | 5/1984 | Kirkland | 209/155 |
| 4,448,679 A | * | 5/1984 | Dilks et al. | 209/155 |
| 4,502,699 A | * | 3/1985 | Mukerji | 277/398 |

(Continued)

FOREIGN PATENT DOCUMENTS

DE   202011110307 U1 *  8/2013
EP       2524732 A1 * 11/2012

(Continued)

*Primary Examiner* — Charles Cooley
(74) *Attorney, Agent, or Firm* — Hodgson Russ LLP (57) ABSTRACT

An apparatus for performing a centrifugal field-flow fractionation is disclosed. In an embodiment of the invention, radial rotary shaft seals are used for sealing the rotating parts of the shaft for carrying out the centrifugal field-flow fractionation and the stationary parts. Furthermore, a separate line is introduced for reducing the pressure differential across these seals. In such way, the driving force driving sample fluid across the seals is reduced, thereby reducing leakage.

12 Claims, 8 Drawing Sheets

(56) References Cited

U.S. PATENT DOCUMENTS

| | | | |
|---|---|---|---|
| 4,657,676 A * | 4/1987 | Keary et al. | 210/198.2 |
| 4,743,227 A * | 5/1988 | Takeuchi | 494/85 |
| 5,052,694 A * | 10/1991 | Lipschitz | 277/388 |
| 7,594,663 B2 * | 9/2009 | Jorgensen et al. | 277/375 |
| 8,192,343 B2 * | 6/2012 | Spiegel et al. | 494/14 |
| 8,475,351 B2 * | 7/2013 | Aizawa | 494/15 |
| 2006/0151403 A1 | 7/2006 | Cardot et al. | |
| 2009/0197752 A1 * | 8/2009 | Spiegel et al. | 494/7 |
| 2012/0220441 A1 * | 8/2012 | Spiegel et al. | 494/10 |
| 2014/0066280 A1 * | 3/2014 | Welz | 494/23 |

FOREIGN PATENT DOCUMENTS

| | | | |
|---|---|---|---|
| EP | 2524733 A1 * | 11/2012 | |
| EP | 2524734 A1 * | 11/2012 | |
| EP | 2524735 A1 * | 11/2012 | |

* cited by examiner

Figure 7B

APPARATUS FOR PERFORMING A CENTRIFUGAL FIELD-FLOW FRACTIONATION COMPRISING A SEAL AND METHOD

TECHNICAL AREA

The invention relates to an apparatus for performing a centrifugal field-flow fractionation as well as to a method for performing a centrifugal field-flow fractionation.

Field-Flow Fractionation (FFF) is a family of unique separation techniques, comprising various different sub-techniques. All FFF techniques utilize the same basic separation principle, but employ different separation fields. Depending on the separation field, the technique is called Flow FFF, Sedimentation FFF, Thermal FFF, etc. FFF is providing fast, gentle and high resolution separations of particulate matter from 1 nm up to 100 μm in liquid media. The sample is separated inside a longitudinal, open flow channel without the presence of any packing or stationary phase inside the channel. The FFF apparatus are typically arranged so that the fluid inside the channel forms a laminar flow with a parabolic stream profile.

The different force fields used, such as liquid flow, centrifugal force, temperature gradient or gravity, are applied perpendicularly to the main flow which transports the sample along the length of the channel. Under the influence of these force fields and counteracting diffusion of the particles, different equilibrium layer heights are formed by the different particle size fractions. Smaller particles, with stronger diffusion, are located higher in the channel in fast stream lines and elute first. Bigger particles with a lower diffusion coefficient are located in slow stream lines and elute later.

Centrifugal FFF has been an important member of the FFF family of techniques since its invention in 1974 by Giddings et al. The first commercial Centrifugal FFF in the 1980s was a system based on a Dupont Sorval Ultracentrifuge, the Model SF3-1000 Sedimentation Field Flow Fractionator. In the 1990s the S-101 Sedimentation FFF was launched. Since 2001 the model CF1000 was provided, which was followed up in 2010 by the new CF2000 Series for nanoparticle separation and characterization.

In centrifugal FFF the separation force is generated by rotating the entire longitudinal, ring-shaped flow channel. As the main flow carries the sample particles along the length of the channel they are affected by the centrifugal field which is generated by the rotation. The larger/heavier particles are more strongly forced towards the radially outer channel wall than the smaller and lighter particles which stay away from the radially outer channel wall. As a result, smaller particles are located in the area of faster stream lines and thus will be eluted first out of the channel, followed by larger particles which are located in the region of slower streamlines. The separation in Centrifugal FFF is based on particle mass (size and density) and because of this allows a very high resolution separation of particles showing only 5% difference in size.

As centrifugal FFF offers a high resolution separation of particles, detectors coupled to the channel are used for further characterization and quantization. Typical detection principles for centrifugal FFF are UV, Dynamic Light Scattering and Static Light Scattering to yield concentration, particle size and elemental distribution.

Although a well-designed system in theory, prior attempts at designing a centrifugal FFF apparatus have failed in practice.

BACKGROUND ART

One such attempt is disclosed in U.S. Pat. No. 4,448,679, on which the preamble of the independent claims of this application is based. This document relates to a centrifugal FFF apparatus in which a liquid to be fractionated is led into a channel present between an inner ring and an outer bowl-shaped structure of a rotor which can be rotated by a motor. During rotation, the liquid to be fractionated is fractionated by the action of the centrifugal force as well as the flow of the liquid through the channel.

A recurring problem with the prior art has been to reduce the leakage of sample fluid introduced into the field-flow fractionation apparatus where the leaks frequently occur at the inlet of the sample fluid into the apparatus: as the rotor rotates whereas the fluid supply is generally stationary, there is a need for a tight seal of the connection between the rotating and the stationary parts of the FFF apparatus. This is particularly challenging due to the need to prevent a leak occurring at an interface between a stationary and a moving part, which is more difficult than just sealing off two stationary parts.

DISCLOSURE OF THE INVENTION

An embodiment of an FFF apparatus according to the invention solves the problem of being able to transfer minimum amounts of liquid through a rotating seal without leakage. The key idea is to avoid axial seals and to instead employ sets of radial seals. Furthermore, and importantly, another key idea is that the pressure differential across each radial seal is minimized which avoids leakage through the seals: there is as a consequence less pressure which could drive a sample liquid across the radial seals, thereby reducing the amount of sample liquid crossing the seal. This is particularly important in radial seals contacting rotating objects as are frequently used in an FFF apparatus as in such an application, a large fraction of the seal contacts the rotating object. Hence, there is a large area available where leaks could occur.

According to an embodiment of the invention, an apparatus for performing a centrifugal field-flow fractionation comprises a shaft having a central axis and conduits along the central axis for sample fluid to pass therethrough. The shaft has an upstream shaft end for the sample fluid to enter into and a downstream shaft end for the sample fluid to exit from the shaft. The shaft carries a rotor between the upstream and the downstream shaft end and is rotatably supported in bearing blocks at both shaft ends so that the rotor and the shaft are rotatable about the axis. The shaft does not have to be a single piece but may consist of several components, which generally makes servicing the shaft easier as in the case of failure of the shaft, only one component needs to be repaired or replaced.

There is a field-flow fractionation channel disposed on the rotor. The field-flow fractionation channel is configured to let the sample fluid pass therethrough and has an upstream channel end for the sample fluid to enter into the channel and a downstream channel end for the sample fluid to exit from the channel. The upstream channel end is connectable in a fluid tight manner to a conduit at the upstream shaft end and a downstream shaft end is connectable in a fluid-tight manner to a conduit at the downstream shaft end.

Further, there is an upstream end cap which fits over the upstream shaft end and can be attached to the bearing block at the upstream shaft end and a downstream end cap which fits over the downstream shaft end and can be attached to the bearing block at the downstream shaft end.

The upstream end cap and the downstream end cap each have a terminal for connection to a line for the sample fluid. The upstream end cap and the downstream end cap each have a further terminal for connection to a line for flushing fluid. The upstream end cap and the downstream end cap each have a first recess and a second recess, each of the first recesses being for accommodation of a first radial rotary shaft seal for sealing the end cap against the shaft and each of the second recesses being for accommodation of a second radial rotary shaft seal for sealing the end cap against the shaft.

In other words, the radial rotary shaft seals are disposed about an axis of rotation of the rotor and are provided to tightly seal the end cap against the shaft. The second radial rotary shaft seal seals between the sample fluid and the flushing fluid whereas the first shaft seal seals between the flushing fluid and the exterior (or potentially another fluid).

Furthermore, according to the invention, each of the second recesses on one side of its second radial rotary shaft seal is in fluid communication with the terminal for connection to the sample fluid line. On the other side of its second radial rotary shaft seal, each of the second recesses is in fluid communication with the terminal for connection to the flushing fluid line, and each of the first recesses on one side of its first radial shaft seal is in fluid communication for connection to the flushing fluid line so that both sides of the second radial rotary shafts are subjected to fluids.

By means of having the connection for introducing the sample fluid into the shaft and by having the possibility of introducing the flushing fluid into the recess, it becomes possible to minimize the pressure differential across the seals which seal the rotating parts against the non-rotating parts. Thus, it becomes possible to reduce the driving force which would otherwise drive the sample fluid through the seal and out of the conduit leading to the FFF channel. In this way, it is avoided to have sample fluid leaking out from the apparatus.

Preferred embodiments of the apparatus according to the invention:

A. may have a pressure differential across the second radial rotary shaft seals (36a/b) that is determined by the difference in pressure arising from 4 to 7 bar sample pressure and about 200 mbar flushing pressure of the sample fluid and the flushing fluid at the respective end cap (28a/b), and the flushing fluid is pressurized so as to control the pressure differential;

B. may have terminals (40a/b) for connection to the line for the sample fluid that are aligned with the central axis when the end caps (28a/b) are attached;

C. may have one or more conduits (54a/b) along said central axis of the shaft (61) that have a diameter sufficiently large for the sample fluid line to extend through the terminal (40a/b) and into the conduit (54a/b);

D. may have a sample fluid line that is inserted into the conduit (54a/b);

E. may have second recesses (37a/b) that are axially remote from the bearing block (24a/b) and first recesses (39a/b) that are axially closer to the bearing block (24a/b);

F. may have first and/or second radial rotary shaft seals 36a/b 38a/b that are free of spiral grooves or helices;

G. may have first recesses (39a/b) on another side of its first radial rotary shaft seal (38a/b) that are each in fluid communication with a further terminal (42a/b) for connection to a drain fluid line or the like;

H. have an upstream end cap a) and a downstream end cap (28b) that are of the same design.

Preferably, the pressure differential across the second radial rotary shaft seal is determined by the difference in pressure of the sample fluid and the flushing fluid at a respective end cap, and the flushing fluid is pressurized so as to control the pressure differential. Here, the pressure differential arises from about 4 to 7 bar sample fluid and about 200 mbar flushing pressure, which is larger than expected. In such way, it becomes possible to minimize the pressure differential, so as to avoid any leakage of sample fluid.

It is preferred that the terminals for connection to the line for the sample fluid are aligned with the central axis when the end caps are attached. Thus, it becomes easier to use a flexible hose or a conduit for introducing the sample fluid into the apparatus as an off-axis terminal would not allow for an easy introduction thereof. Also, this avoids adding an extra variation of the pressure to the sample fluid which would otherwise occur if a terminal was used which is off-axis with respect to the axis of rotation: in such a case, a rotation would lead to a sinusoidal variation in the sample fluid pressure, which would negatively affect the quality of the FFF performed. Thus, by the preferred design, the quality of the outcome of the centrifugal FFF as well as the tightness of the seal is improved.

It is furthermore preferred that at least one of the conduits along said central axis of the shaft has a diameter sufficiently large for the sample fluid line to extend through the terminal and into the conduit. In this way, the sample fluid line can be easily introduced into the shaft. Thereby, the sample fluid is released from the sample fluid line further inside the apparatus, which in turn means that there is less of a risk of sample fluid leaking out of the apparatus.

It is preferred that the sample fluid line is inserted into the conduit. As an advantage, this reduces the risk of leakage occurring in a manner similar to the previous mechanism.

Preferentially, the second recesses are axially remote from the bearing block and the first recesses are axially closer to the bearing block. This allows for an easier design of the end cap as well as for an easier handling of the apparatus: if the first recess was axially more remote from the bearing block than the second recess, it would be necessary to have a more complicated pattern of connecting the fluid lines. Thus, setting up the apparatus would become more difficult. Also, it becomes easier to replace the seals.

It is additionally preferred that the first and/or second radial rotary shaft seals are free of spiral grooves or helices. In such a way, the rotary shaft seals have less of a tendency to leak. Also, wear of the seals during use is reduced as radial rotary shaft seals which are free of spiral grooves or helices have good wearing properties, which ensures that they keep their advantageous sealing properties during use.

Additionally, it is preferable that each of the first recesses on the other side of its first radial rotary shaft seal is in fluid communication with a further terminal for connection to a drain fluid line or the like. This leads to a further potential for improvement in leakage tightness as the pressure differential across these two lines can also be minimized.

Preferably, the upstream end cap and the downstream end cap are of the same design. This makes producing the field-flow fractionation channel more affordable as only one type of end cap is needed.

The problem is also solved by a method for performing a centrifugal FFF, which comprises the following steps:

A flow of a sample fluid is provided to an upstream terminal of an apparatus for performing a centrifugal field-flow fractionation. The flow of sample fluid is passed through a field-flow fractionation channel. The flow of sample fluid is conveyed away from the downstream terminal of the apparatus. A flow of a flushing fluid is provided to an upstream terminal of the apparatus. A flow of flushing fluid is provided to a downstream terminal of the apparatus. The flow of sample fluid is sealed from the flow of flushing fluid at the upstream terminal by means of a radial seal, and the flow of sample fluid is sealed from the flow of flushing fluid in a downstream terminal by means of a radial seal.

Again, the use of the radial seals together with there being two fluids connected by them avoids any leakage of sample fluid from the apparatus. The mechanism is essentially the same as described in the above.

Preferred embodiments of a method according to the invention may include the step of pressurizing the flushing fluids so as to reduce the difference in pressures of the flushing fluid and of the sample fluid at the upstream terminal (40*a*) and the difference in pressures of the flushing fluid and of the sample fluid at the downstream terminal (40*b*). In addition, it may be that the step the flow of sample fluid to the upstream terminal (40*a*) of the apparatus (10) for performing a centrifugal field flow fractionation and/or the step of conveying the flow of sample fluid away from the downstream terminal (40*b*) of the apparatus (10) comprises introducing a sample fluid line into a conduit (54*a*/b) in a shaft (61) of the apparatus (10), the conduit (54*a*/b) extending along a central axis of the shaft (61).

It is preferred that the method additionally comprises the step of pressurizing the flushing fluids so as to reduce the difference in pressures of the flushing fluid and of the sample fluid at the upstream terminal and the difference in pressures of the flushing fluid and of the sample fluid at the downstream terminal. As an advantage, this leads to lower leakage as there is even less of a pressure differential across a radial seal which would otherwise drive the sample fluid out of the apparatus, thereby leading to leakage.

Preferably, there are the additional steps of providing the flow of sample fluid to the upstream terminal of the apparatus for performing a centrifugal field-flow fractionation and of conveying the flow of sample fluid away from the downstream terminal of the apparatus comprising the introducing of a sample fluid line into a conduit in a shaft of the apparatus. In particular, the conduit shall extend along a central axis of the shaft.

As an advantage, this leads to a reduced leakage as the sample fluid line can be introduced further into the shaft which avoids the potential of leakage compared to the case where it was only introduced into the apparatus to a lesser extent.

DETAILED DESCRIPTION

A preferred way of carrying out the invention will now be described with reference to the accompanying drawings.

Figure 1:
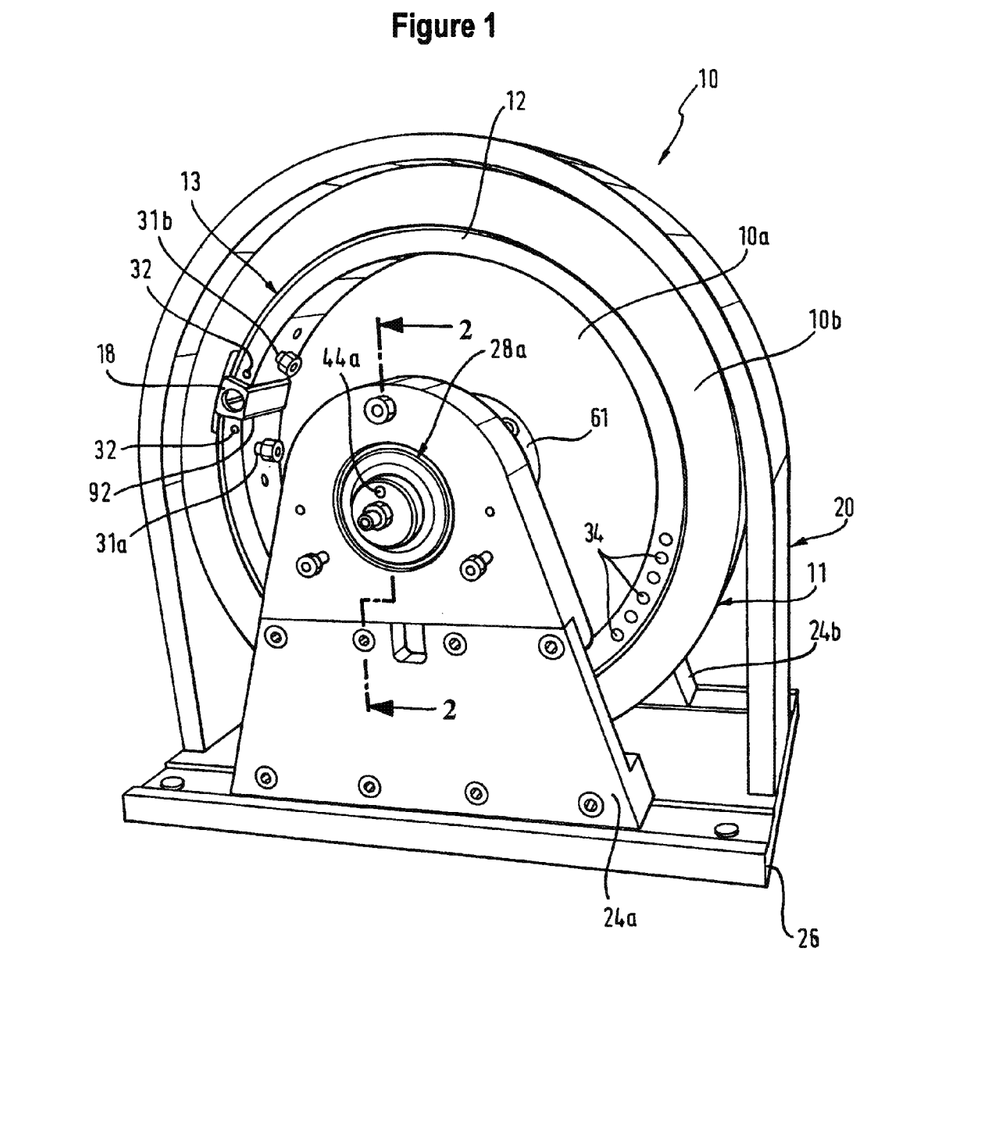
FIG. 1: shows an assembled centrifugal field-flow fractionation apparatus according to the invention.

FIG. 1 shows an assembled centrifugal field-flow fractionation apparatus 10 according to the invention. It should be noted that end caps 28*a*/b, which will be described in more detail further below, are missing in this Figure but will be attached before operation of the FFF apparatus. The drawing shows a rotor 10*a* which can be rotated about a shaft 61 (shown in more detail in FIG. 2). The shaft, in turn, comprises several individual pieces. The rotor 10*a* is driven by a DC electric motor (not shown). The rotor 10*a* has a generally bowl-shaped structure, with a hub 10*b* as a radially inner part and a rim 11 as a radially outer part. The hub is essentially disc-shaped, with a circular outer circumference. The outer rim 11 is annular, with a rectangular cross-section, and extends circumferentially around the hub 10*b* as well as axially beyond the hub 10*b*. Thus, the overall shape of the rotor 10*a*, when viewed perpendicularly to the plane of the hub 10*b* and in the direction of the shaft 61, is circular. Within the hub 10*b* and adjacent to the outer rim 11, there is an attachment mechanism, such as a threaded hole (not shown) for insertion of a bolt and attachment of the fractional field flow channel, as will be apparent from the below. The rim and the hub can be made of one unitary piece, or of separate elements which are later assembled.

On an inner circumferential surface of an outer rim 11 of rotor 10*a*, a holder 12 is attached to the rotor 10*a*. A structure 13, which is described below, constitutes the fractional field flow channel.

The holder 12 has a generally annular shape with an interrupted segment 92 and, so as to reduce its weight, yet provide the mechanical strength needed, is made of an aluminium manganese zinc copper alloy. When the structure 13 is assembled with the holder 12 and the rotor 10*a*, a wedge 18 is inserted into the interrupted segment 92. The holder 12 further comprises two holes 32. These holes can be used for extracting wedge 18 from its inserted position. Further holes 34 are present in the holder 12 at a position radially opposite the interrupted segment 92. These holes 34 are balancing bores the location and volume of which are ideally determined by means of dynamic balancing. They prevent an imbalance occurring during operation of the FFF apparatus.

Outside the rotor 10*a*, a separate covering element 20 in the form of an inverted U is provided. It extends around a periphery of the rotor 10*a* and prevents a person from accidentally touching the spinning rotor 10*a*. This element 20 is made of a strip of material, preferably metal, and preferably has an extension along the axial direction of the rotor-carrying shaft 61 beyond both the front and the rear of the rotor 10*a* as seen along the axial direction of the shaft 61.

Figure 2:
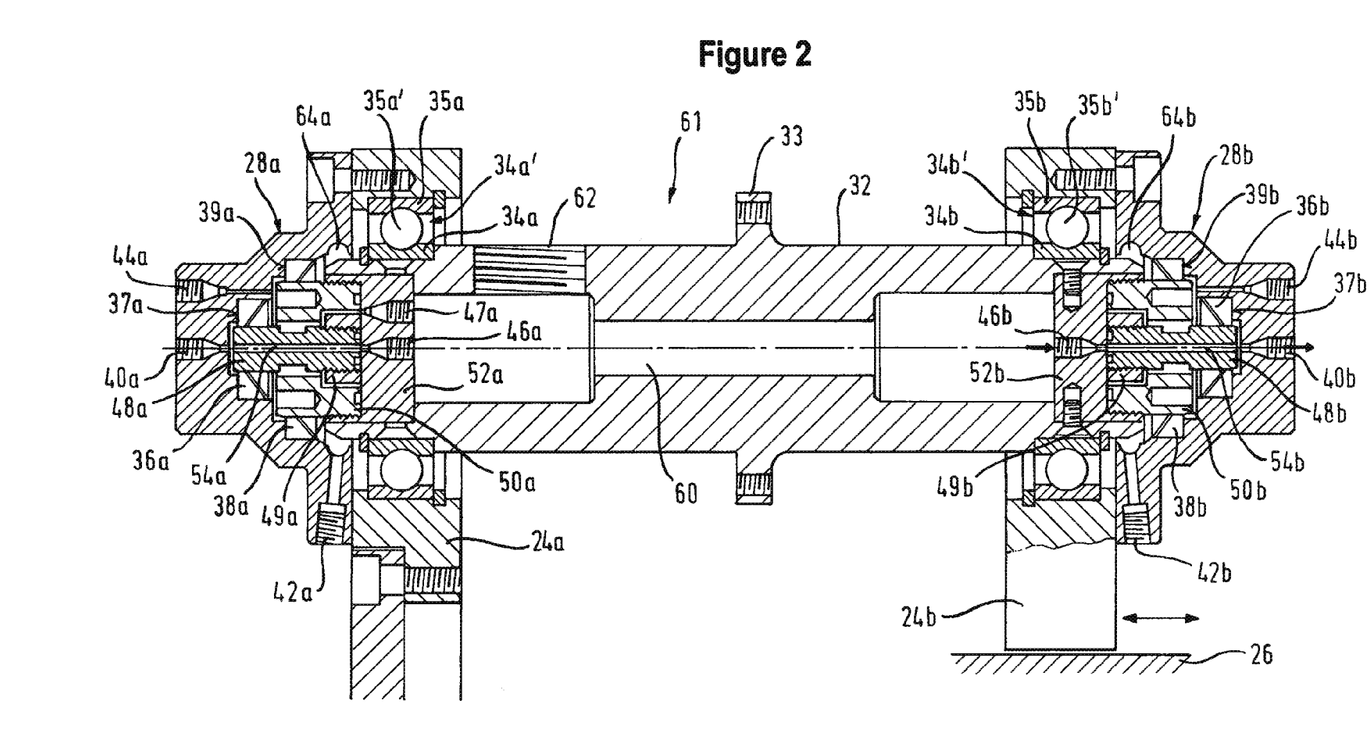
FIG. 2: shows a cross-sectional view of the seal and bearing structure of the field-flow fractionation apparatus of FIG. 1, taken along the section line 2-2 in FIG. 1.
Figure 3:
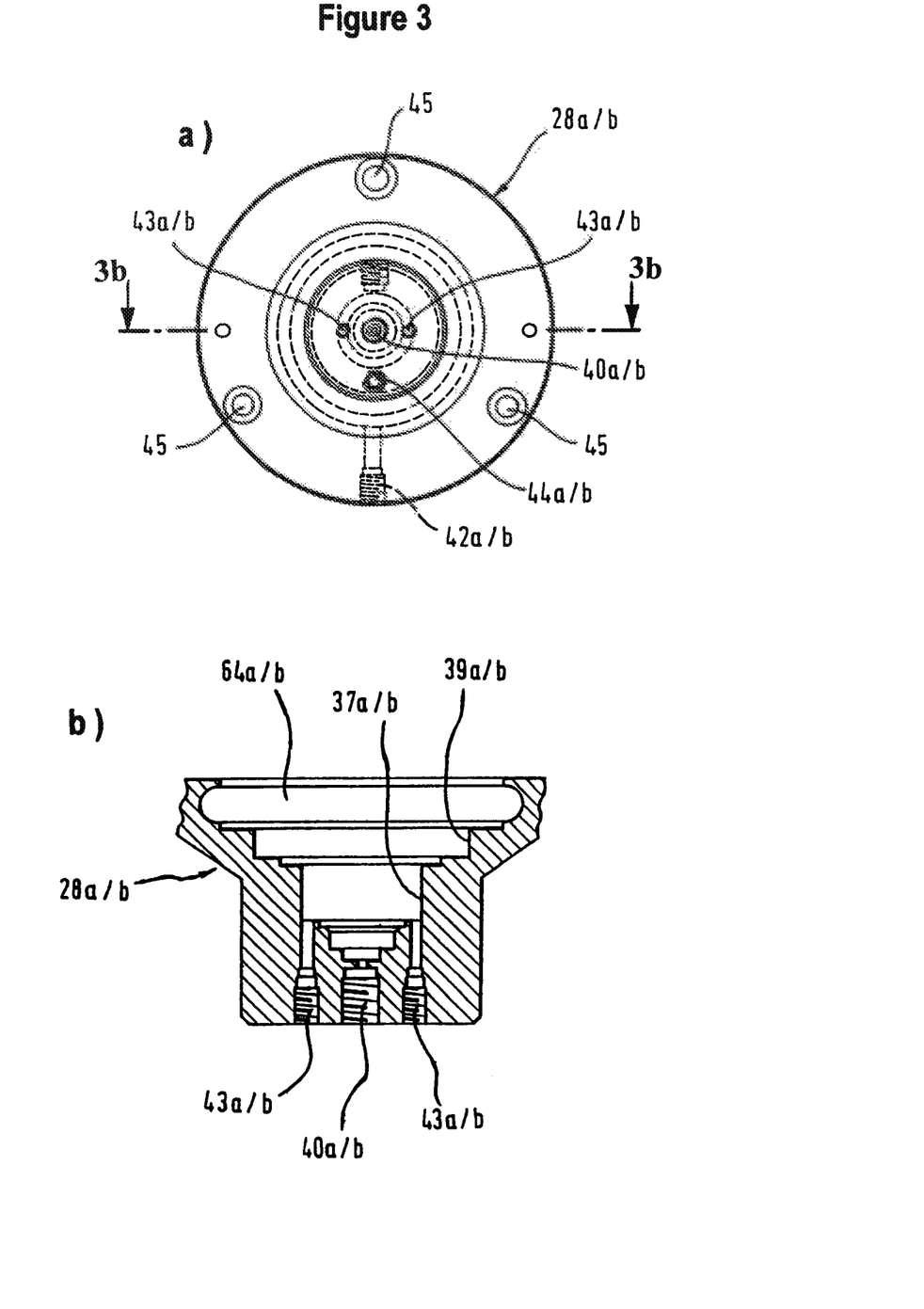
FIG. 3*a*: shows a plan view of the end cap of FIG. 2.
FIG. 3*b*: shows a cross-sectional view of the end cap of FIG. 2, taken along the section line 3*b*-3*b* in FIG. 3*a*.

The rotor 10*a* is carried by shaft 61 which passes into end caps 28*a* and 28*b* (in short referred to as 28*a*/b) (FIGS. 2 and 3). In the centre of these end caps 28*a*/b, connecting pieces 48*a*/b (FIG. 2) for letting the sample fluid pass into or out of the centrifugal field-flow fractionation apparatus is provided. These connecting means 48*a*/b can preferably be a hollow tube. The terminal 40*a*/b itself takes the form of a threaded bore, with the bore extending through the end cap (with the threads not extending all the way).

Connecting pieces 48*a*/b are connected to another means 31*a*/b for letting fluid pass into or out of the centrifugal field-flow fractionation channel 13. The means 31*a*/b for letting fluid pass into and out of the channel 13 is disposed on an inner circumference of the holder 12 adjacent the interrupted segment 92 for accommodating the wedge 18. In the interest of avoiding a multiplicity of different parts, it can be embodied in the form of tubing with standard attachments.

The shaft 61 passes through and is rotatably supported in an opening disposed in a bearing block 24*a*/b, and extends further into end cap 28*a*/b. At least one of the bearing blocks 24*a*/b consists of two individual elements. The bearing blocks 24a/b are themselves supported on a base 26. Preferably, the position of the bearing blocks relative to one another can be adjusted, for instance by having one of them, such as bearing block 24b, displaceably connected to the base 26, as schematically indicated in FIG. 2. The other bearing block 24a is fixed in its location relative to the base 26.

Alternatively, both blocks could be adjustable, or the position adjustment could be achieved through different means, such as a split base.

FIG. 2 shows in more detail the support structure for supporting the shaft 61 as well as the structure inside the end caps 28a/b. It can be seen that the two bearing blocks 24a/b are supported on the base 26, where block 24a is fixedly supported by the base 26 whereas block 24b is displaceably supported (the direction of the displacement being indicated by an arrow) on the base 26. On each of the bearing blocks 24a/b, end caps 28a/b are fixed by suitable means such as screws or bolts or the like. These end caps 28a/b each generally have the shape of a cup. At the base end of each of these "cups", two terminals 40a/b and 44a/b are provided, which are each penetrating the cup and take the shape of threaded holes. These terminals 40a/b, 44a/b each have a diameter which decreases when moving in the axial direction of the shaft from the outside towards the hub (at 33 in FIG. 2), i.e. from the closed to the open end of the end caps 28a/b. The terminals are designed for introducing fluid lines such as flexible conduits such as hoses or flexible tubing. Each terminal 40a/b is arranged along the central axis of the respective end cap 28a/b. The end caps are placed so that the central axes of their openings coincide with the axis of rotation of the shaft 61. Axially offset towards the rim of the caps 28a/b, where the caps are attached to the supports 24a/b, there are disposed additional terminals 42a/b extending along a generally radial direction. These terminals extend into bores through the thickness of the rim of the end cap 28a/b. They are, again, designed for an exchange of liquid between the interior and the exterior of the cap, in this case for introducing a drain fluid line and draining fluid.

In the assembled apparatus, the end caps 28a/b are arranged such that the central axes of their openings are aligned with the central axis of an opening in the respective bearing block 24a/b. The opening of the bearing block 24a/b serves to accommodate roller bearings which support the central element 32 of shaft 61.

Roller bearings 34a'/b' consist of inner and outer raceways 34a/b and 35a/b, respectively, and a plurality of roller elements 35a'/b', respectively, disposed between them. The raceways 34a/b and 35a/b are made of steel whereas the roller elements 35a'/b' are made from ceramics. The roller elements 35a'/b' all have a spherical shape. In the present embodiment, both roller bearings 34a/b are single row deep grooved roller bearings. Although not recommended for this application, they are standard parts and can be ordered from suppliers such as INA/FAG, NTN, SKF or others. The roller elements 35a'/b' are made of a material which differs from that of the inner and outer raceways 34a/b and 35a/b so as to reduce friction and avoid lubrication during use. Whilst the roller bearings 34a/b may be provided with a minimal amount of oil as a lubricant upon assembly of the FFF apparatus, such as one or two drops per bearing, they are not lubricated during operation, even after prolonged use.

Each roller bearing 34a'/b' is each fixed both with respect to the shaft 61 and its support in bearing block 24a/b so that there is no axial clearance. Upon assembly of the FFF apparatus, possible axial clearance can be eliminated by displacing one of the bearing blocks relative to the other, or by accordingly adjusting a split base, if present, or by other suitable means known in the art.

As was stated in the above, the shaft 61 comprises several individual components, namely, those denoted by reference signs 32, 48a/b, 50a/b, and 52a/b. The shaft 61 has the overall shape of a generally rotationally symmetric longitudinal element with an axis of symmetry running approximately along its longitudinal direction. A central shaft element 32 is arranged at the longitudinal centre of shaft. It consists of a sleeve having a hollow inner portion 60 arranged along the axis of the shaft. At about the longitudinal centre region of the shaft portion 32, the hollow inner portion 60 is preferably constricted, i.e. the wall of the hollow inner portion 60 becomes thicker, which ensures a lower weight and higher stability of the shaft 61. At this location, however, the shaft could also be solid. At the radially outer periphery at a position corresponding to the preferably constricted or possibly solid portion, the shaft has a circumferential flange 33 with means such as threaded bores for attaching the rotor 10a. This also corresponds to approximately midway axially between the supports 24a and 24b. This particular position is chosen in accordance with the shape of the rotor so that it has the highest stability, which means that it will more likely withstand the forces due to the spinning rotor 10a, and will generate the lowest imbalance when the rotor is spinning. Further, the hollow inner portion 60 is open to an exterior at a portion 62 connecting the hollow inner portion 60 of the central shaft element 32 to an exterior.

At both longitudinal ends of the central shaft portion 32, first connecting pieces 52a/b are provided in a cylindrical recess in central shaft portion 32. The first connecting pieces 52a/b take the form of a cylindrical plate with a recess portion. The recess is generally cylindrical but exhibits an irregular cylinder surface in that the cylinder surface has a plurality of segments which are enlarged in diameter and accordingly provide a passage for fluid. On the radial outside, the recess portions leave a ring-shaped web which is preferably provided with a thread. In the assembled state, the cylindrical recess portions are directed to the outside, away from the shaft element 32. The recess portions do not penetrate through the first connecting pieces 52a/b. Thus, the recesses are only present at one axial side of the first connecting piece 52a/b.

Placed on and along the axis of rotation of these cylindrical plates, terminals 46a/b are provided in the form of threaded bores. In the assembled disposition of the first connecting pieces 52a/b, these bores have a diameter which decreases when moving through the terminals to the outside, away from the shaft element 32. At one side of the first connecting piece 52a/b, the terminal 46a/b opens up into the cylindrical recess portion with a diameter larger than that of the terminals. It is evident from FIG. 2 that the terminals 46a and 46b are axially aligned with a bore that is located axially outside of the terminals and provided in second connecting pieces 48a/b. At least one of the first connecting pieces 52a/b is connected to the other side of the plate at one off-centre portion of the first connecting piece 52a (i.e. not connecting piece 52b) by means of a further terminal 47a taking the form of a threaded bore. However, in the interest of economical manufacturing, the first connecting pieces 52a and 52b could both exhibit the off-centre connection by means of a further terminal. In this manner, there would be only one type of connecting piece. If the further terminal 47a is not in use in one of the first connecting pieces 52a or 52b, it could be blocked by a blind plug.

Second connecting pieces 48a/b are assembled with ring-shaped elements 49a/b, preferably by means of a thread as shown in FIG. 2, and the resulting sub-sub-assembly is inserted, for instance press-fitted, into a recess provided in the third connecting pieces 50a/b. As shown in FIG. 2, however, the irregular cylinder surface of recess portion in third connecting pieces 50a/b leaves areas of fluid communication.

The result is a sub-assembly of elements 48a/b, 49a/b and 50a/b. The elements of this sub-assembly are so designed and arranged that their end faces which, in the assembled state of the sub-assembly, are oriented towards the cylindrical recess in the first connecting piece 52a/b, are flush.

Third connecting pieces 50a/b preferably carry a thread on the outside. If they do, the sub-assembly is screwed into the recessed portions of first connecting pieces 52a/b. In the absence of a thread, the sub-assembly would otherwise be fitted into place, for instance by press-fitting or gluing.

Alternatively, the recess portion of first connecting piece 52a/b could exhibit the shape of a ring instead of a cylinder. In this case, elements 49a/b would be of one piece with first connecting piece 52a/b and both, second connecting piece 48a/b and third connecting piece 50a/b could simply be screwed into first connecting piece 52a/b. Fluid communication would then be provided through a radial gap between element 49a/b and third connecting piece 50a/b. The end faces of the second and third connecting pieces could also be axially offset relative to one another.

The resulting assembly of elements 48a/b, 49a/b, 50a/b and 52a/b is then inserted into and retained in the central shaft portion 32 by means of screws, or bolts, as shown in FIG. 2 for first connecting piece 52b to the right-hand side. It should be noted that all connecting pieces 48a/b, 50a/b and 52a/b are aligned with the axis of the shaft 61 they constitute.

The second connecting piece 48a/b takes the form of a cylinder with a passage connecting the centres of its end faces, one of the end faces being aligned with terminal 46a/b of first connecting piece 52a/b and the other with terminal 40a/b of the end cap 28a/b, and acts as a tube. The passage is preferably a central conduit 54a/b which is aligned with both terminal 46a/b of first connecting piece 52a/b and terminal 40a/b of the end cap 28a/b. The second connecting piece 48a/b is preferably recessed on the outside surface so as to provide a fluid chamber. The axial length of the second connecting piece 48a/b is greater than the axial length of the third connecting pieces 50a/b. Third connecting pieces 50a/b, in turn, have an axial length greater than the web of cylindrical recess portions in first connecting pieces 52a/b. As a result, the radially innermost connecting pieces 48a/b project furthest in the axial direction, and the third connecting pieces 50a/b which are located radially further outside, project less. The amount of the axial projection is sufficient to present a sealing surface for seal rings 38a/b and 36a/b.

The first seal rings 38a/b are located radially outside of third connecting pieces 50a/b, and are sealingly disposed between these first connecting pieces 50a/b and the neighbouring wall of end caps 28a/b. They are accommodated in recesses 39a/b of the end cap. The first seal rings 38a/b surround first connecting pieces 50a/b in a fluid-tight manner. Similarly, second seal rings 36a/b are located radially outside of second connecting pieces 48a/b, accommodated in recesses 37a/b of the end cap and are sealingly disposed between these second connecting pieces 48a/b and the wall of end caps 28a/b. The seal rings 38a/b and 36a/b are rotary shaft seals which are free of spiral grooves or helices.

The end cap 28a/b preferably lies flush against bearing block 24a/b and retained in place so that there is a fluid tight connection between them. Tightness against leakage of fluid could, however, also be obtained through other means known in the art.

FIG. 3a shows a plan view and FIG. 3b a cross-sectional view of end cap 28a/b along line B-B in FIG. 3a. It is apparent that terminal 40a/b extends through the end wall of end cap 28a/b along the central axis of the essentially rotationally symmetric end cap 28a/b. Additionally, in FIG. 3a, three through-holes 45, preferably countersunk bores, are shown. They serve for connecting the end cap 28a/b to the respective bearing block 24a/b and are meant for the insertion of a screw or any other suitable fastening means. FIG. 3a also shows terminal 44a/b.

Particularly FIG. 3b shows second recess 37a/b and first recess 39a/b in the end cap 28a/b, both the second 37a/b and the first recess 39a/b having an essentially cylindrical shape that is coaxial with the bore of terminal 40a/b. The radial dimension, i.e. the diameter of second recess 37a/b is smaller than that of first recess 39a/b. Both recesses 37a/b and 39a/b are immediately adjacent to one another, with the first recess 39a/b being located axially further towards the opening of the "cup" of cup-shaped end cap 28a/b, i.e. the second recess 37a/b is axially remote from the bearing block 24a/b whereas the first recess 39a/b is axially closer to the bearing block 24a/b Still axially further towards the opening of the cup, there is a further (third) recess 64a/b which takes the shape of a cylinder with a circularly shaped portion disposed around it such that its radially outermost surface is curved like the segment of a torus. The radial dimension of the third recess 64a/b is even bigger than that of the second 37a/b and first recess 39a/b. The third recess 64a/b is preferably also arranged coaxially with the second 37a/b and first 39a/b recess but other arrangements are possible. The bore of terminal 42a/b opens into third recess 64a/b, as may be taken from FIG. 3a.

FIGS. 3a and 3b further show two through holes 43a/b, which are partially threaded. They open into recess 37a/b and serve so as to be able to push seal ring 38a/b out of recess 37a/b.

End cap 28a/b is dimensioned relative to the assembly of elements 48a/b, 49a/b, 50a/b and 52a/b so that, when end cap 28a/b carrying sealing rings 36a/b and 38a/b is placed over the assembly, there are axial gaps between the axially outer end face of second connecting piece 48a/b and the inner, axially outermost surface of recess 37a/b of end cap 28a/b as well as between the axially outer end face of third connecting piece 50a/b and the inner, axial end face of recess 39a/b of end cap 28a/b. In the assembled state of the FFF apparatus, the latter gap is thus located between the two sealing rings 36a/b and 38a/b.

Terminal 44a/b is in fluid communication with, and preferably opens straight into, the axial gap between the first and second seal rings 36a/b and 38a/b and second and third connecting pieces 48a/b and 50a/b. Terminal 42a/b leads to the gap between seal rings 38a/b and the fluid-tight interface between the end cap 28a/b and the bearing block 24a/b, i.e. each of the first recesses 39a/b on the other side of its first radial rotary shaft seal 38a/b is in fluid communication with terminal 42a/b. Terminal 47a leads to the enlarged portions of the cylinder surface of the recess in third connecting piece 50a/b or to the radial clearance between connecting piece 52a/b and connecting piece 50a/b. Terminals 40a/b and conduits 54a/b are designed such that their diameters are sufficiently large to allow for a sample fluid line 98a/98b such as standard flexible tubing to extend through the terminals 40a/b and into the conduits 54a/b. The bore of terminals 46a/b, conversely, does not permit tubing to pass. In the present embodiment, the upstream and the downstream end cap 28a/b both have the same design.

Figure 4:
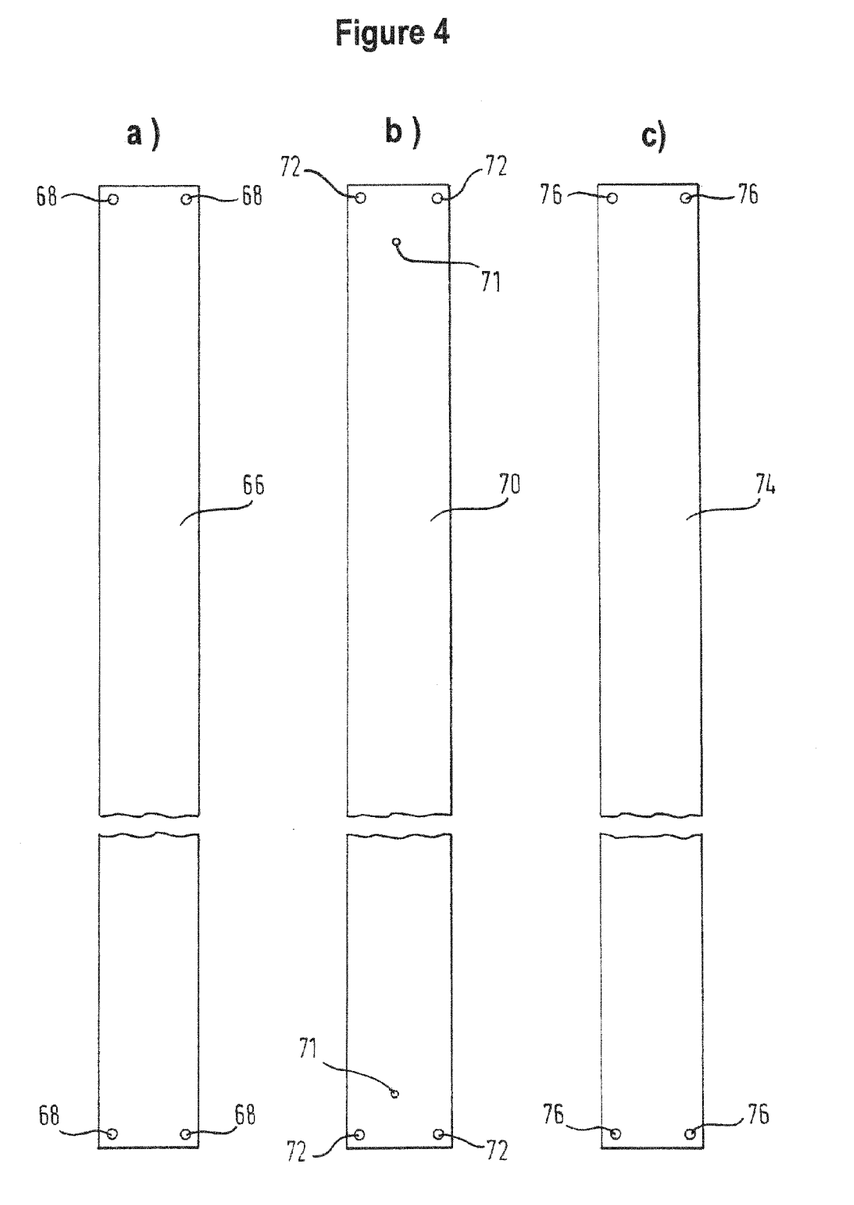
FIGS. 4*a*-*c*: show the spacers used in the apparatus according to FIG. 1.

FIGS. 4a to c show strips for use in defining the FFF channel 13.

Figure 5:
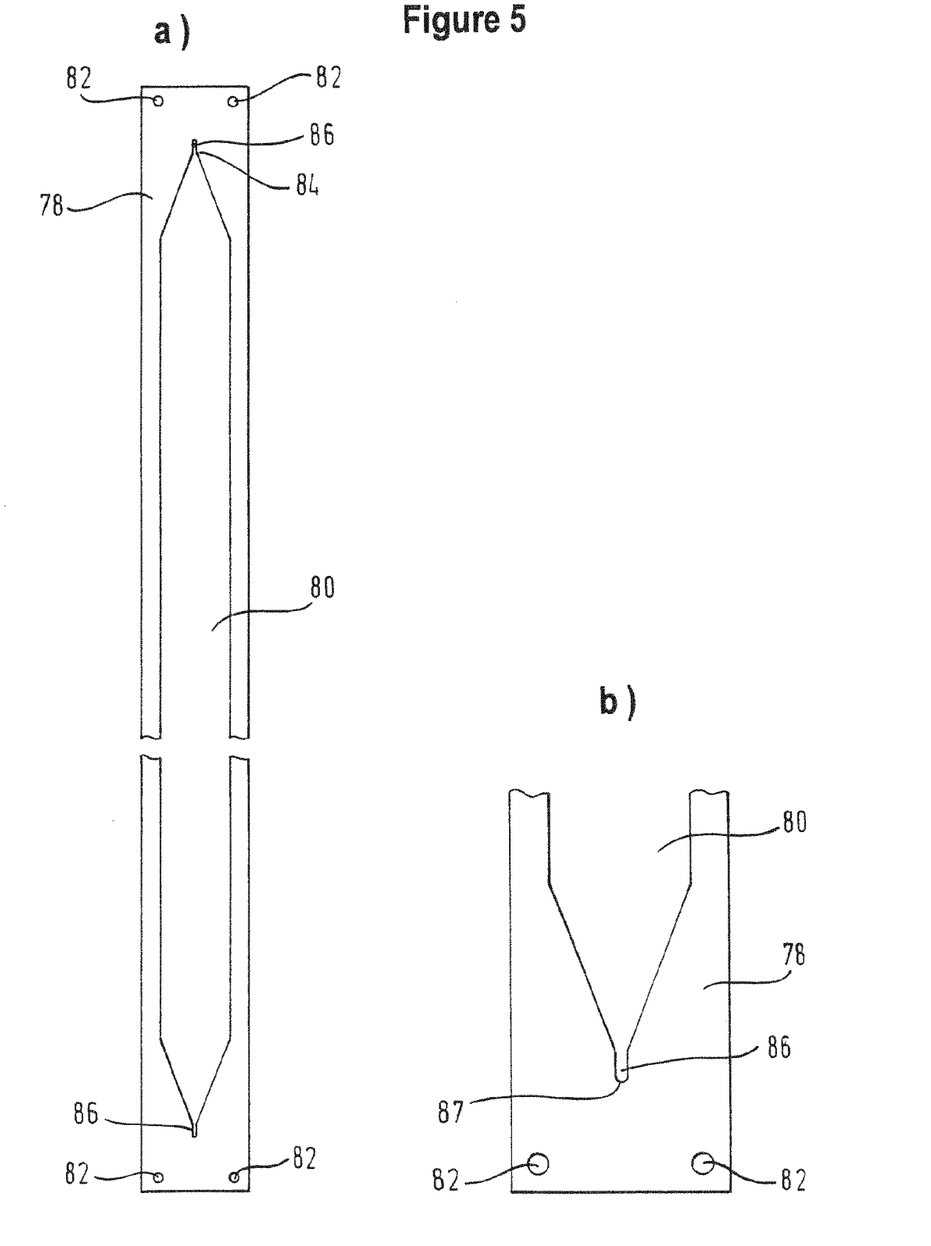
FIGS. 5*a*-*b*: show the foil used in the apparatus according to FIG. 1

The strips are stacked onto each other between the holder 12 and, radially outside of the stack, the rim 11. In the stack, an inner spacer 70 lies adjacent a channel-defining foil 78 (FIG. 5) which, in turn, lies adjacent an outer spacer 66. Optionally, a compensation strip 74 is placed between outer spacer 66 and rim 11.

FIG. 4a shows the outer spacer 66 to be used between the foil 78 (FIG. 5) defining the channel 13 and the rim 11 of the rotor 10a. Outer spacer 66 is made of a Mylar polyester foil, i.e. a foil made of biaxially oriented polyethylene terephthalate, or a metal sheet and, at least on the side facing foil 78, has an average surface roughness of 1.5<Ra<1.7, and preferably Ra=1.6, the surface roughness being measured in accordance with DIN EN ISO 4287:2010-07 as the arithmetic average of absolute values, for instance by means of a laser scanning type camera and providing the roughness in μm. This way of defining the surface roughness is used throughout the whole of this present description unless otherwise stated.

Four holes 68 are disposed on corners of the otherwise generally rectangular strip 66. The thickness of strip 66 is significantly less than 1 mm and preferably app. 250 μm, and its surface facing foil 78 is completely scratch-free so as to aid in sealing the channel 13. Strip 66 is checked for scratches by visual inspection, i.e. by an optical measurement.

FIG. 4b shows an inner spacer 70 which is disposed between the holder 12 and the foil 78 defining the channel 13. Again, similarly to spacer 66, it has a generally rectangular form, with holes 72 disposed at the four corners of the strip. Whilst the axial, or transverse distance between the holes 68, 72 at one longitudinal end of the spacers 66 and 70 is identical, the circumferential, or longitudinal distance between holes 72 of inner spacer 70 is shorter than the corresponding distance between holes 68 of outer spacer 66. The difference in circumferential distance is adapted to the inner diameter of the rim 11 so that holes 68 and 72 coincide once spacers 66, 70 with foil 78 placed therebetween assume the radius of curvature defined by the diameter of rim 11. The inner spacer 70 can be made of the same materials as the other spacer 66.

Further, holes 71 are arranged on the longitudinal axis of inner spacer 70. As illustrated, these holes 71 have a circular cross-section; however, any other cross-section can be used. They serve for letting a sample fluid enter and exit the FFF channel 13. At least on the side facing foil 78, the surface roughness of spacer 70 is 1.5<Ra<1.7, and preferably Ra=1.6. In the illustrated embodiment, spacer 70 is made of stainless steel of grade 1.4310 for use in springs. The spacer 70 has a thickness of significantly less than 1 mm and preferably app. 250 μm.

FIG. 4c shows the compensation strip 74. The compensation strip 74 is optionally disposed immediately between the rim 11 and the outer spacer 66. Similar to the other strips in FIGS. 4a and 4b, it has four holes 76 disposed at the respective corners of the otherwise rectangular strip 74, placed so that their location coincides with that of holes 68, 72 once compensation strip assumes the radius of curvature defined by the inner diameter of rim 11. Compensation strip 74 is also made of stainless steel of grade 1.4310, with a thickness of less than 1 mm and preferably app. 250 μm.

FIG. 5 shows the foil 78 for defining the field-flow fractionation channel 13. The foil 78 has a generally rectangular form with four holes 82 being disposed at the corners of the foil 78. They are placed so that their location coincides with that of holes 68, 72, 76 once foil 78 is placed in the stack adjacent rim 11. In conjunction, these holes serve to align the elements of the stack on the holder 12. So as to assist in compressing the stack, the holes can also be oblong, with the longitudinal direction of the holes running in the circumferential direction of the rim 11 and the holder 12.

Foil 78 has a thickness which is adapted to the fluids to be fractionated. In the illustrated embodiment, the thickness is app. 250 μm, but it can also have a thickness such as app. 100 μm to app. 800 μm. The foil 78 is made of Polytetrafluoroethylene (PTFE) which is more commonly known as "Teflon", a brand name of E.I. du Pont de Nemours and Company. However, any other material such as a fluoroelastomer can be used as long as it is a self-sealing material, i.e. a material which automatically forms a good seal against leakage, and as long as it is resilient. The surface roughness of both faces of the foil is 1.5<Ra<1.7, and preferably Ra=1.6. The surface on both faces has to be scratch-free to aid in sealing.

In the central part of the foil 78, there is provided a recess 80 penetrating the foil. The recess defines the entire geometry of the FFF channel 13, i.e. thickness, length, width, diverging and converging sections. Recess 80 is disposed completely inside foil 78, i.e. the material of foil 78 completely surrounds it. The holes 82 are not connected to the recess 80 defining the channel 13. The shape of the recess 80 can be described as a longitudinally stretched hexagon, with slots 86 (FIG. 5b) longitudinally extending away from the farthest corners of the hexagon. The remaining four corners are disposed on the corner of what can be described as a rectangle. Alternatively, the shape could be described as a longitudinal rectangle with a triangle each joined to the short sides of the rectangle, and the apexes of the triangles terminating in the slots 86. At each end of the slots 86, there is an opening 87 in the form of a segment of a circle, with the diameter of the circle defining the opening 87 being at least equal to the width of the slots 86, and preferably being larger than the width of the slots 86. In an assembled apparatus, these openings 87 are aligned with holes 71 of inner spacer 70, with holes 71 being larger than openings 87.

Figure 6:
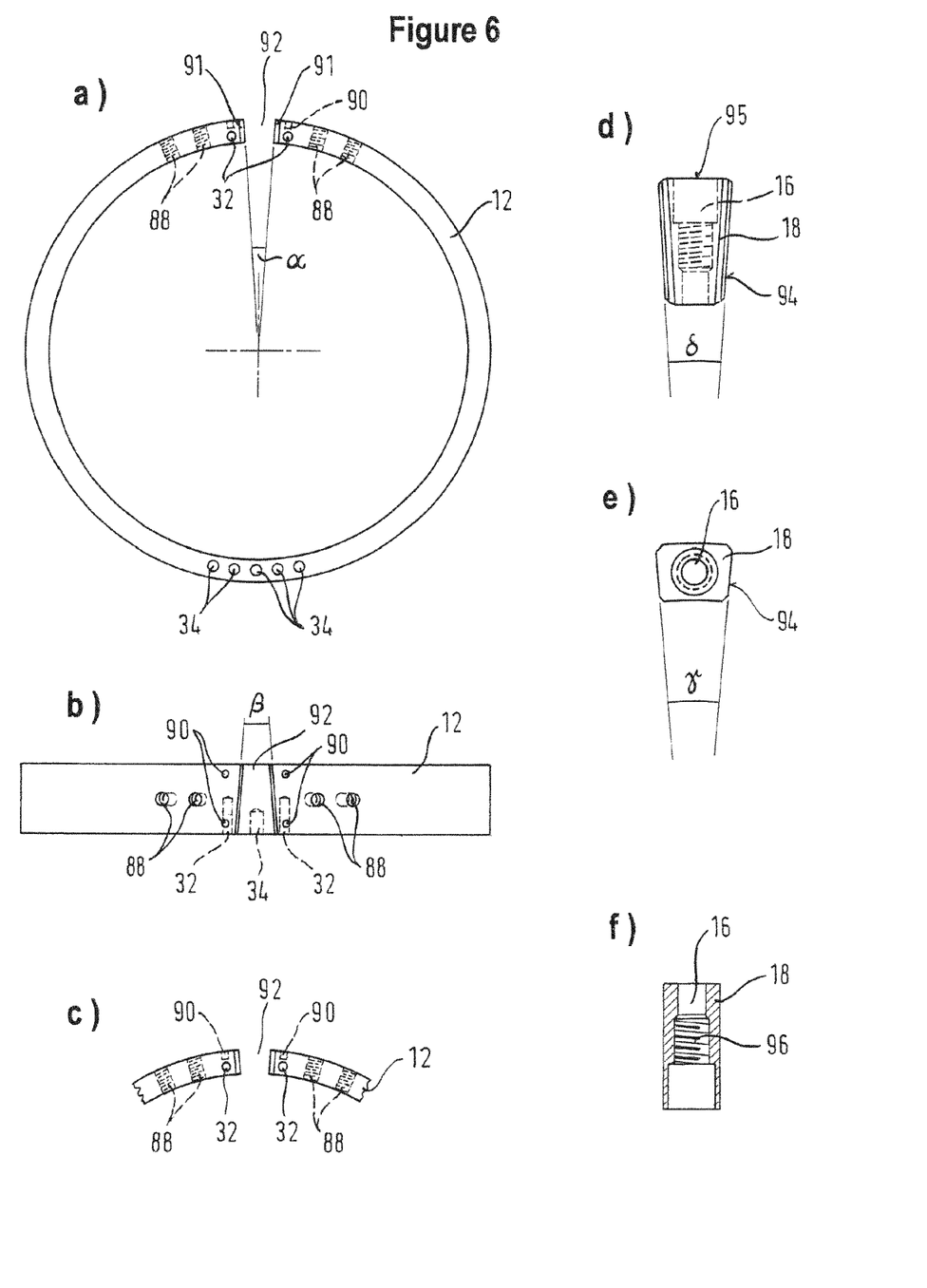
FIGS. 6*a*-*c*: show the holder of the FFF channel of FIG. 1.
FIGS. 6*d*-*f*: display the wedge for holding the holder of FIG. 1 in place.
Figure 7A:
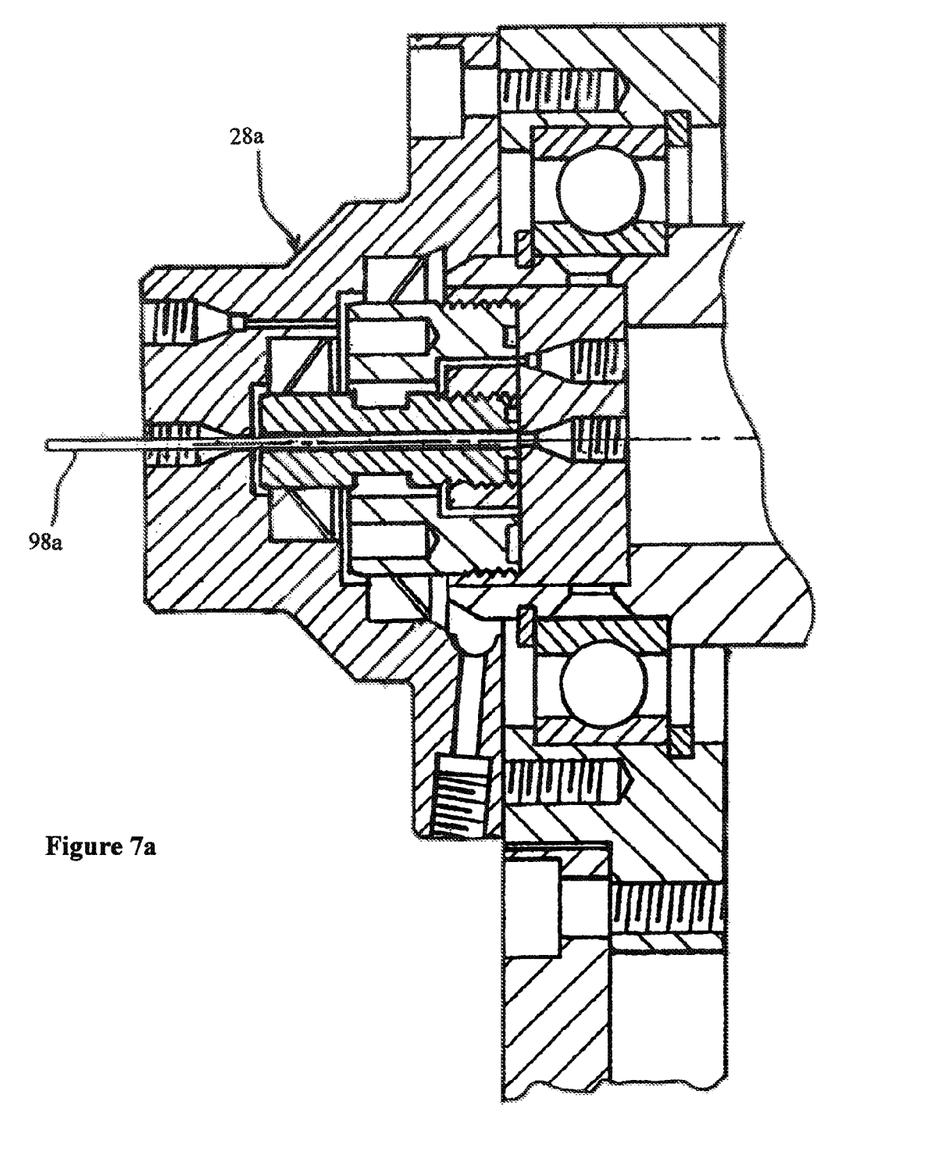
FIG. 7*a* is an enlarged portion of FIG. 2, showing a sample fluid line 98*a*.
Figure 7B:
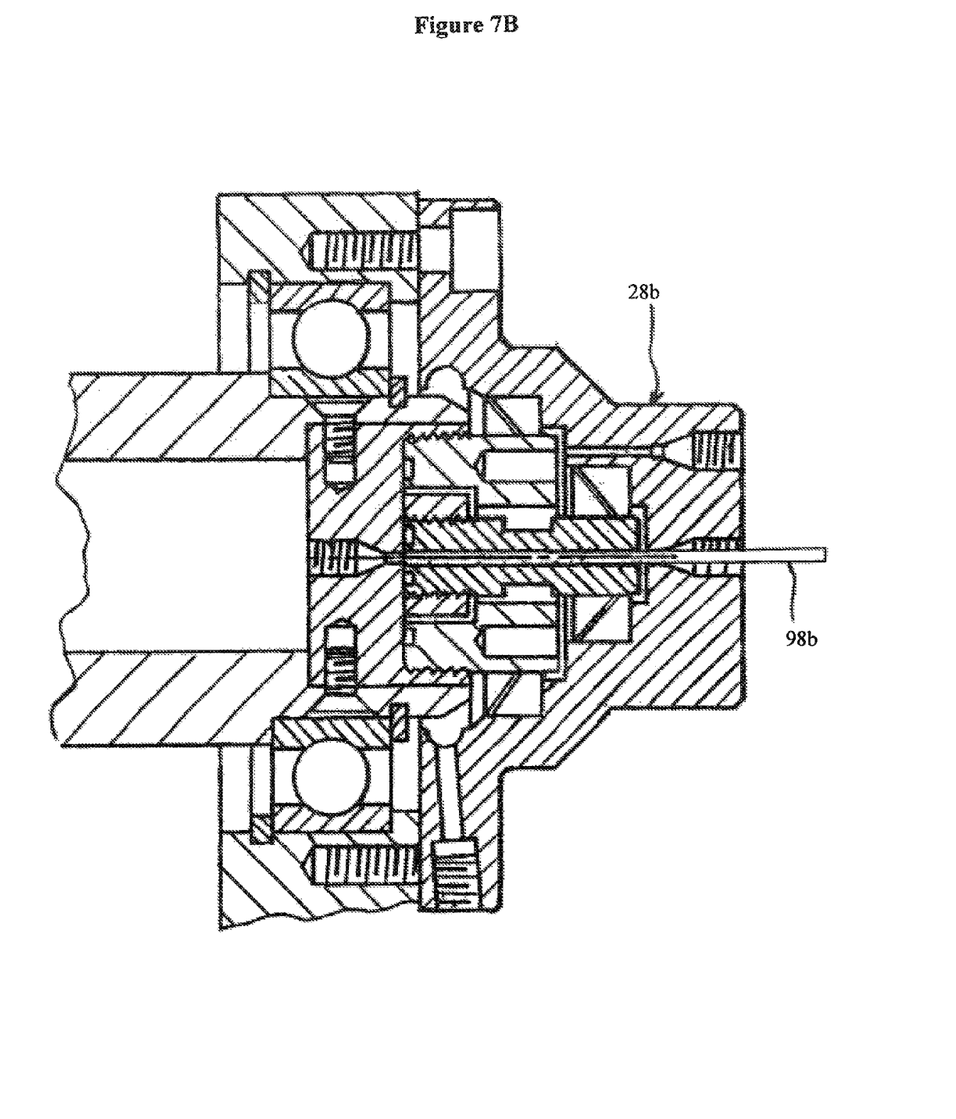
FIG. 7*b* is an enlarged portion of FIG. 2 showing a sample fluid line 98*b*.

FIGS. 6a to c show the holder 12 in detail. FIG. 6a shows a side, or axial view of the holder 12. The holder 12 is formed of an aluminium zinc manganese copper alloy which has been hard coated. Its outside surface is smooth, with the surface roughness on the outside being 0.35<Ra<0.45, preferably being app. Ra=0.4. It consists of a generally rectangular strip which has been bent into the shape of an annulus or circle having an interrupted segment 92. Interrupted segment 92 serves to accommodate wedge 18 (FIGS. 6d, 6e, 6f).

As can be seen from the centre of the annulus or circle, the end faces 91 of the holder 12 adjacent the interrupted segment 92 subtend an angle α of app. 10°, preferably 10°±0.05°, which is also the angle the surfaces of the end faces 91 of holder 12 subtend when viewed along the axis of the annulus. At least one recess, and preferably one or more holes 34, is disposed opposite the interrupted segment 92 of the holder 12, in the illustrated embodiment five bores 34. By having one or more recesses in this position, it is avoided that the field-flow fractionation apparatus is out of balance during operation. Any number of holes can be used as long as their number and design is such that the reduction in imbalance is achieved.

Holes 90 are disposed at both sides of the interrupted segment 92. They serve for bolts, screws, pins or other suitable means for connecting the holes 68, 72, 76, 72 in the foil 78 and in the spacers 68, 72, 76 to the radially peripheral surface of holder 12. Axial bores 32 can be disposed in the holder 12, as illustrated, for helping in removing wedge 18, as will be discussed further below.

Threaded through holes 88 are placed circumferentially spaced further away from the interrupted segment 92 than holes 90 and 32. Through holes 88 serve to let a fluid flow enter into and exit from the FFF channel 13 when the apparatus is in use. These holes 88 thus extend through the thickness of the holder 12. One hole 88 next to each side of the interrupted segment 92 would be sufficient for a particular type of channel 13. In the illustrated embodiment, however, two holes are provided next to each side so as to be able to use the holder with two channel types of different length. Naturally, the number of holes could also be larger than two.

In use, one hole 88 on one side of interrupted segment 92 is aligned with one hole 71 in order to allow sample fluid to enter into the channel 13. One hole 88 on the other side of interrupted segment 92 is aligned with hole 71 at the opposite end of channel 13 in order to allow sample fluid to exit from the channel 13.

FIG. 6b shows a radial view of holder 12 when looking at interrupted segment 92 from radially outside of the holder 12. It becomes apparent that the interrupted segment 92 is also tapered along the axial direction of holder 12. Once the FFF apparatus is assembled, the interrupted segment 92 becomes narrower due to the taper when moving in the direction of hub 10b. This is also the depth direction of threaded holes 32 away from the axially peripheral surface and into the body of holder 12. The angle of taper β subtended by the end faces of interrupted segment 92 in this direction is app. 8° and preferably 8°±0.05°. The surface roughness of the end faces 91 defining the interrupted segment 92 is 0.35<Ra<0.45, and preferably Ra=0.4.

FIG. 6c shows another view of the interrupted segment 92 when viewed along the axial direction and is essentially a close-up view of the corresponding part of FIG. 6a.

FIGS. 6d to f show a wedge 18 to be inserted into interrupted segment 92. The wedge 18 is configured to be inserted and wedged into the interrupted segment 92 of the holder so as to force the holder 12 and spacers 68, 72, 76 and foil 78 defining the FFF channel 13 against the inner circumference of the rim 11 of rotor 10a.

Wedge 18 is made of an aluminium zinc manganese copper alloy which has been hard coated by a polytetrafluoroethylene (PTFE) coating. The coating preferably has a thickness of between 20 to 25 μm. Also preferably, the surface quality of the wedge is as noted above with respect to holder 12.

The wedge 18 has a pair of generally opposed surfaces 94. Each surface has the shape of an oblong rectangle, the longer edges of the rectangles being essentially parallel to the axial direction and the shorter edges being essentially parallel to the radial direction of the FFF apparatus. The surfaces 94 of the pair are inclined with respect to one another in two directions.

Firstly, they are inclined so that in the inserted position of the wedge 18 and in an axial view, both surfaces 94 extend along radial beams with an angular offset approximately corresponding to the angular circumferential dimension of interrupted segment of the holder 12. Their angle of inclination is thus such that they fit tightly with the surfaces defining the end faces 91 of holder 12. In particular, in the currently preferred embodiments, the angle of inclination γ with respect to one another is app. 8° and preferably 8°±0.05°.

Secondly, the wedge 18 is designed such that the surfaces 94 are inclined with respect to one another so that they subtend an angle δ when viewed along the axial direction of the assembled FFF apparatus. The angle δ is designed such that the wedge 18 circumferentially displaces the holder 12 by a predetermined amount when it is axially advanced into the interrupted segment. This can appropriately be effected with the assistance of a tool. In this particular preferred embodiment, the angle of axial taper subtended by the end faces 94 is app. 10° and preferably δ=10°±0.05°.

Along the direction of the wedge 18 which is parallel to the longer edges of the rectangular surfaces 94, i.e. parallel to the axial direction of the rotor 10a when the wedge 18 is inserted into the interrupted segment 92, there is a throughhole in the form of a stepped bore 16 (FIG. 6f). The diameters of the stepped bore 16 increase when moving from the end of the bore opening in the smaller end face of the wedge 18 to the end of the bore opening in the larger end face of the wedge 18, "large" and "small" in this context referring to the overall area of the respective end faces. The bore 16 also contains a thread 96 for introducing a screw by means of which the wedge can be removed from the corresponding bore in the rotor 10a. In the present embodiment, the wedge 18 has an axial length which is slightly less than the axial dimension of holder 12.

BEST MODE OF OPERATING THE APPARATUS

In the following, the currently preferred way of operating the previously described apparatus 10 will be described, starting from the assembly of the apparatus.

First, the hub 10b is attached to flange 33 of the shaft. Then, or in parallel, the inner spacer 70, then the foil 78, followed by the outer spacer 68 and optionally the compensation strip 74 are stacked on the holder 12 such that the holes 82, 68, 72, 76, and 90 are aligned with one another. This will serve to automatically align holes 88, 71 and openings 87 with one another to let a sample fluid enter into and exit from the recess 80 defining the FFF-channel 13. The resulting stack is then connected by suitable means such as bolts. Then, holder 12 together with the assembled FFF channel 13 is inserted into the interior of the rim 11 of the rotor 10a.

Wedge 18 is inserted into interrupted segment 92 of holder 12 by means of a suitable tool such as a gear puller or extractor which is applied to the surface of the hub facing away from the holder, reaches through the stepped bore 16 of the wedge and acts on the end face 95 of the wedge. The act of wedging the wedge 18 into the interrupted segment 92 can then be effected by a screwing action of the gear puller whilst leaving the thread 96 in the bore 16 of the wedge 18 and the thread in the corresponding hole of the hub 10b unused. Otherwise, due to the high forces needed, wedging the wedge 18 into the interrupted segment 92 might damage or destroy these threads. It is the general idea to use the tool to apply this force between the axial end face 95 of the wedge 18 and a corresponding surface of the hub 10b of the rotor 10a such that the wedge 18 is wedged into the interrupted segment 92, thereby wedging apart holder 12 and forcing the channel 13 against rim 11. This is done at such a position that the bore 16 of the wedge 18 is aligned with the corresponding bore in the hub 10b to enable a screw, a bolt or other suitable means to attaching the wedge 18 to the hub 10b and secure the wedge in its wedged position.

Once the wedge 18 has been wedged into the interrupted segment 92, it is secured to the rotor by means of a screw inserted through hole 16 and screwed into the corresponding threads of the bore in the rotor 10a. However, it should be noted that the screw is under normal circumstances of operation not needed. The wedge 18 and the interrupted segment 92 are designed so that, in normal operation, the wedge will not be displaced. The function of the screw is simply a safety precaution in case the FFF apparatus experiences unusual shocks which may cause the wedge to be dislocated. Also, if the wedge was not held in place, a problem might arise when turning on the FFF apparatus: initially, when the holder 12 is not firmly pressed against rim 11 due to the centrifugal force, there would only be a small force holding the wedge 18 inside the interrupted segment 92. Thus, the forces during turning on might act as to dislodge the wedge 18. As it is, at least at this stage, not firmly secured inside the interrupted segment 92, it might as a consequence be ejected from the apparatus, thereby potentially hitting bystanders and equipment.

The first, second and third connecting means as well as the end caps are assembled as described above.

After the rotor has been assembled in this manner, means for supplying and extracting field-flow fractionation liquid (sample fluid) to and from the shaft 61 are connected by suitable means, such as fitting flexible tubing by means of standard tubing adapters so that the tubing extends from terminal 46*a* to one of holes 88 and from the other of holes 88 to terminal 46*b*. This establishes a connection between the shaft 61 and the field-flow fractionation channel 13 defined by the foil 78.

Afterwards, suitable means, such as flexible tubing, for supplying field-flow fractionation liquid (sample fluid) to and from the rotor are applied. The flexible tubing is introduced through terminal 40*a* into conduit 54*a* for introducing the fluid to be fractionated. Further flexible tubing is introduced through terminal 40*b* into conduit 54*a* for removing the fractionated fluid.

Here, it should be noted that the means such as the flexible tubing extends into the conduits 54*a/b* until close to, but not up to contact with the first connecting pieces 52*a/b*.

Flushing fluid connection lines are connected to terminals 44*a/b* and drain fluid lines are connected to terminals 42*a/b*.

Terminals 47*a/b* are closed by plugging them with a blind terminal connector, i.e. one which does not permit fluid to pass. Flushing fluid is supplied through terminals 44*a/b*. It fills the space between the two seal rings in the end cap, i.e. the space downstream of the second seal ring 36*a/b* and upstream of the first seal ring 38*a/b*. The pressure of the flushing fluid is controlled so that its pressure corresponds to the pressure of the sample fluid at the respective terminal 40*a/b*. In this manner, the pressure difference across the second seal rings 36*a/b* is minimized, preferably to less than 0.05 bar, and even minimal loss of sample fluid is prevented. It has turned out to be particularly advantageous if the pressure differential across the second seal rings is minimized by having 4 to 7 bar pressure of the sample fluid and about 200 mbar pressure of the flushing fluid and that by means of controlling the flushing pressure, the pressure difference across the first seal ring 38*a/b* is controlled, thereby sealing the flow of sample fluid. Since the first seal rings 38*a/b* seal a liquid from a gaseous space, fluid is more likely to leak there than at the second seal rings 36*a/b* which seal to liquid-filled spaces from each other. Possible excess flushing fluid will thus leak across the first seal rings 38*a/b* and is then drained through terminals 42*a/b*.

Alternatively, terminal 47*a* and/or terminal 47*b* could be connected to a discharge line for the flushing fluid. If terminal 47*a/b* is connected in this manner, the flushing fluid is supplied to terminals 44*a/b*. The space "downstream" of the seal rings 36*a/b* is filled, as in the previously-described alternative, but here the flushing fluid is permitted to flow past the second seal ring 36*a/b* and to leave the space through the one or both of terminals 47*a* and 47*b* which is connected to a discharge line. This alternative facilitates operation of the FFF apparatus since control of the flushing fluid pressure is less intricate.

In the thus assembled apparatus 10, the motor is made to turn the shaft 61 about its axis. The motor is, as was mentioned previously, a DC electric motor. It is supplied by an external AC to DC power supply or by another type of power supply, e.g. a battery. The AC to DC power supply is suitable for use in the country the apparatus is to be used in that it is capable of converting that country's AC mains voltage and frequency into the correct DC power for use in the motor driving the FFF apparatus. Also, sample fluid and flushing fluid are led into and conducted out of the FFF apparatus at the respective inlets and outlets. The sample fluid thus passes through the field flow fractionation channel 13.

The invention claimed is:

1. An apparatus (10) for performing a centrifugal field flow fractionation comprising:

a shaft (61) having a central axis and conduits (54*a/b*) along said central axis for sample fluid to pass therethrough, the shaft (61) having an upstream shaft end for the sample fluid to enter into and a downstream shaft end for the sample fluid to exit from the shaft (61), the shaft (61) carrying a rotor (10*a*) between the upstream and the downstream shaft ends and being rotatably supported in bearing blocks (24*a/b*) at both said shaft ends so that the rotor (10*a*) and the shaft (61) are rotatable about the axis, a field flow fractionation channel (13) on the rotor (10*a*), the field flow fractionation channel (13) being configured to let the sample fluid pass therethrough and having an upstream channel end for the sample fluid to enter into the channel and a downstream channel end for the sample fluid to exit from the channel (13), the upstream channel end being connectable in a fluid-tight manner to a conduit (54*a*) at the upstream shaft end and the downstream channel end being connectable in a fluid-tight manner to a conduit (54*b*) at the downstream shaft end, an upstream end cap (28*a*) which fits over the upstream shaft end and can be attached to the bearing block (24*a*) at the upstream shaft end and a downstream end cap (28*b*) which fits over the downstream shaft end and can be attached to the bearing block (24*b*) at the downstream shaft end, the upstream cap end (28*a*) and the downstream end cap (28*b*) each having a terminal (40*a/*b) for connection to a line for the sample fluid, the upstream end cap (28*a*) and the downstream end cap (28*b*) each having a further terminal (44*a/*b) for connection to a line for flushing fluid, the upstream end cap (28*a*) and the downstream end cap (28*b*) each having a second recess (37*a/*b) and a first recess (39*a/*b), each of the second recesses (37*a/*b) being for accommodation of a second radial rotary shaft seal (36*a/*b) for sealing the end cap (28*a/*b) against the shaft (61) and each of the first recesses (39*a/*b) being for accommodation of a first radial rotary shaft seal (38*a/*b) for sealing the end cap (28*a/*b) against the shaft (61), each of the second recesses (37*a/*b) on one side of its second radial rotary shaft seal (36*a/*b) being in fluid communication with the terminal (40*a/*b) for connection to the sample fluid line and on the other side of its second radial rotary shaft seal (36*a/*b) being in fluid communication with the terminal (40*a/*b) for connection to the flushing fluid line, and each of the first recesses (39*a/*b) on one side of its first radial rotary shaft seal (38*a/*b) being in fluid communication with the terminal (44*a/*b) for connection to the flushing fluid line, so that both sides of the second radial rotary shaft seals (36*a/*b) are subjected to fluids.

2. The apparatus (10) according to claim 1, wherein the pressure differential across the second radial rotary shaft seals (36*a/*b) is determined by the difference in pressure arising from 4 to 7 bar sample pressure and about 200 mbar flushing pressure of the sample fluid and the flushing fluid at the respective end cap (28a/b), and the flushing fluid is pressurized so as to control the pressure differential.

3. The apparatus (10) according to claim 1, wherein the terminals (40a/b) for connection to the line for the sample fluid are aligned with the central axis when the end caps (28a/b) are attached.

4. The apparatus (10) according to claim 3, wherein at least one of the conduits (54*a/b*) along said central axis of the shaft (61) has a diameter sufficiently large for the sample fluid line to extend through the terminal (40a/b) and into the conduit (54a/b).

5. The apparatus (10) according to claim 4, wherein the sample fluid line is inserted into the conduit (54a/b).

6. The apparatus (10) according to claim 1, wherein the second recesses (37a/b) are axially remote from the bearing block (24a/b) and the first recesses (39a/b) are axially closer to the bearing block (24a/b).

7. The apparatus (10) according to claim 1, wherein the first and/or second radial rotary shaft seals (26a/b, 38*a/b*) are free of spiral grooves or helices.

8. Previously Presented) The apparatus (10) according to claim 1, wherein each of the first recesses (29a/b) on the other side of its first radial rotary shaft seal (38a/b) is in fluid communication with a further terminal (42a/b) for connection to a drain fluid line.

9. The apparatus (10) according to claim 1, wherein the upstream end cap (28*a*) and the downstream end cap (28*b*) are of the same design.

10. A method of performing a centrifugal field flow fractionation, the method comprising the following steps:

providing a flow of sample fluid to an upstream terminal (40*a*) of an apparatus (10) for performing a centrifugal field flow fractionation, passing the flow of sample fluid through a field flow fractionation channel (13), conveying the flow of sample fluid away from a downstream terminal (40*b*) of the apparatus (10), providing a flow of flushing fluid to an upstream terminal (44*a*) of the apparatus (10), providing a flow of flushing fluid to a downstream terminal (44*b*) of the apparatus (10), sealing the flow of sample fluid from the flow of flushing fluid at the upstream terminal (40*a*) by means of a radial seal (36*a*), and sealing the flow of sample fluid from the flow of flushing fluid at the downstream terminal (40*b*) by means of a radial seal (36*b*).

11. A method according to claim 10, further comprising the step of pressurizing the flushing fluids so as to reduce the difference in pressures of the flushing fluid and of the sample fluid at the upstream terminal (40*a*) and the difference in pressures of the flushing fluid and of the sample fluid at the downstream terminal (40*b*).

12. A method according to claim 10, wherein the step of providing the flow of sample fluid to the upstream terminal (40*a*) of the apparatus (10) for performing a centrifugal field flow fractionation and/or the step of conveying the flow of sample fluid away from the downstream terminal (40*b*) of the apparatus (10) comprises introducing a sample fluid line into a conduit (54*a/b*) in a shaft (61) of the apparatus (10), the conduit (54*a/b*) extending along a central axis of the shaft (61).

\* \* \* \* \*